(12) United States Patent  
Heck et al.

(10) Patent No.: US 7,915,421 B2  
(45) Date of Patent: Mar. 29, 2011

(54) METHOD FOR PREPARING PHENYL ACETIC ACID DERIVATIVES

(75) Inventors: Rainer Heck, Freiburg (DE); Michael Justus, Schaffhausen (CH); Roland Müller, Aarau (CH); Thomas Otten, Zürich (CH); Martin Rettig, Friesenheim (DE)

(73) Assignee: Cilag Ltd., Schaffhausen (CH)

( * ) Notice: Subject to any disclaimer, the term of this patent is extended or adjusted under 35 U.S.C. 154(b) by 1079 days.

(21) Appl. No.: 10/556,268

(22) PCT Filed: May 13, 2004

(86) PCT No.: PCT/CH2004/000292  
§ 371 (c)(1),  
(2), (4) Date: Dec. 4, 2006

(87) PCT Pub. No.: WO2004/101540  
PCT Pub. Date: Nov. 25, 2004

(65) Prior Publication Data  
US 2007/0123564 A1    May 31, 2007

(30) Foreign Application Priority Data  
May 14, 2003  (CH) ........................ 0847/03

(51) Int. Cl.  
C07D 295/12    (2006.01)
(52) U.S. Cl. ........................................ 546/234
(58) Field of Classification Search .......... 546/234  
See application file for complete search history.

(56) References Cited

U.S. PATENT DOCUMENTS

| 5,312,924 A | 5/1994 | Grell et al. |
| 6,143,769 A | 11/2000 | Grell et al. |
| 7,148,355 B2 * | 12/2006 | Ray et al. ............... 546/234 |

FOREIGN PATENT DOCUMENTS

| CA | 2111851 | * | 7/1993 |
| EP | 0207331 A1 | | 1/1987 |
| EP | 0965591 A1 | | 12/1999 |
| WO | WO93/00337 A1 | | 1/1993 |
| WO | WO2004/018442 A1 | | 3/2004 |

OTHER PUBLICATIONS

Nucleofuge Web deifinition, chemiPlus p. 1 (2010).*  
Nucleofuge Web definition, Chem dictionary p. 1 (2010).*  
Stn. Exhibit I p. 1 (2010).*

* cited by examiner

Primary Examiner — Celia Chang  
(74) Attorney, Agent, or Firm — Hammer & Associates, P.C.

(57) ABSTRACT

Method for preparing (S)(+)phenyl acetic acid derivatives having the general formula (I):

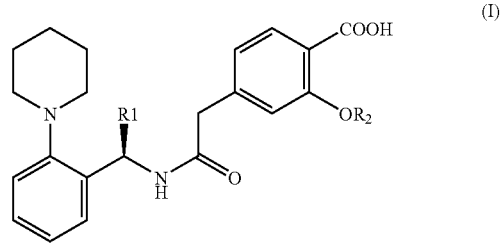

wherein $R_1$ is a linear or branched alkyl group with 1-6 carbon atoms or substituted benzyl group, and $R_2$ is methyl, ethyl or propyl group said method, characterised in that a compound of the general formula (II):

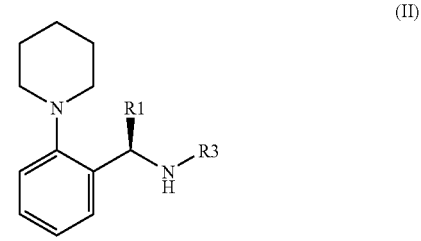

wherein $R_1$ is as given above, and $R_3$ is a nucleofuge, or a suitable salt of a compound of the general formula (II) is reacted with a compound having the general formula (III):

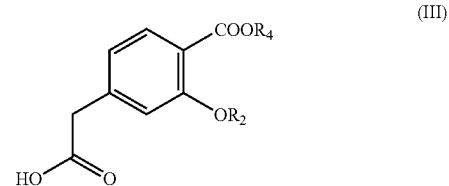

wherein $R_2$ is as given above, and $R_4$ is hydrogen or a nucleofuge that can be removed hydrolytically, and the protective group $R_4$ that may be present, may be subsequently removed hydrolytically.

12 Claims, 5 Drawing Sheets

METHOD FOR PREPARING PHENYL ACETIC ACID DERIVATIVES

The present invention concerns a technique for preparing phenyl acetic acid derivatives, especially, the (S)(+)-2-ethoxy-4-[N-[1-(2-piperidino-phenyl)-1-alkyl]-amino-carbonyl-methyl]-benzoic acid and (S)(+)-2-ethoxy-4-[N-[1-(2-piperidino-phenyl)-1-benzyl]-amino-carbonyl-methyl]-benzoic acid. Of these compounds, (S)(+)-2-ethoxy-4-[N-[1-(2-piperidino-phenyl)-3-methyl-1-butyl]-amino-carbonyl-methyl]-benzoic acid is important, since it is well-known as a pharmaceutically active substance under the name of Repaglinid.

Repaglinid and the related compounds are described, for instance, in EP 0 589 874 and EP 0 965 591. These compounds are effective in particular for reducing blood sugar. In the conventional methods of preparation, the appropriate primary amine i.e. a (S)-1-(2-piperidino-phenyl)-1-alkylamine, or (S)-1-(2-piperidino-phenyl)-1-benzylamine, is reacted with an appropriate, substituted, phenyl acetic acid. Thereafter in the compound, thus obtained, the carboxyl group, bonded to the phenyl ring and protected as an ester group, is converted into the free carboxyl group.

BRIEF DESCRIPTION OF THE DRAWINGS

For the purpose of illustrating the invention, there is shown in the figures a form that is presently preferred; it being understood, however, that this invention is not limited to the precise arrangements and instrumentalities shown.

Figure 1:
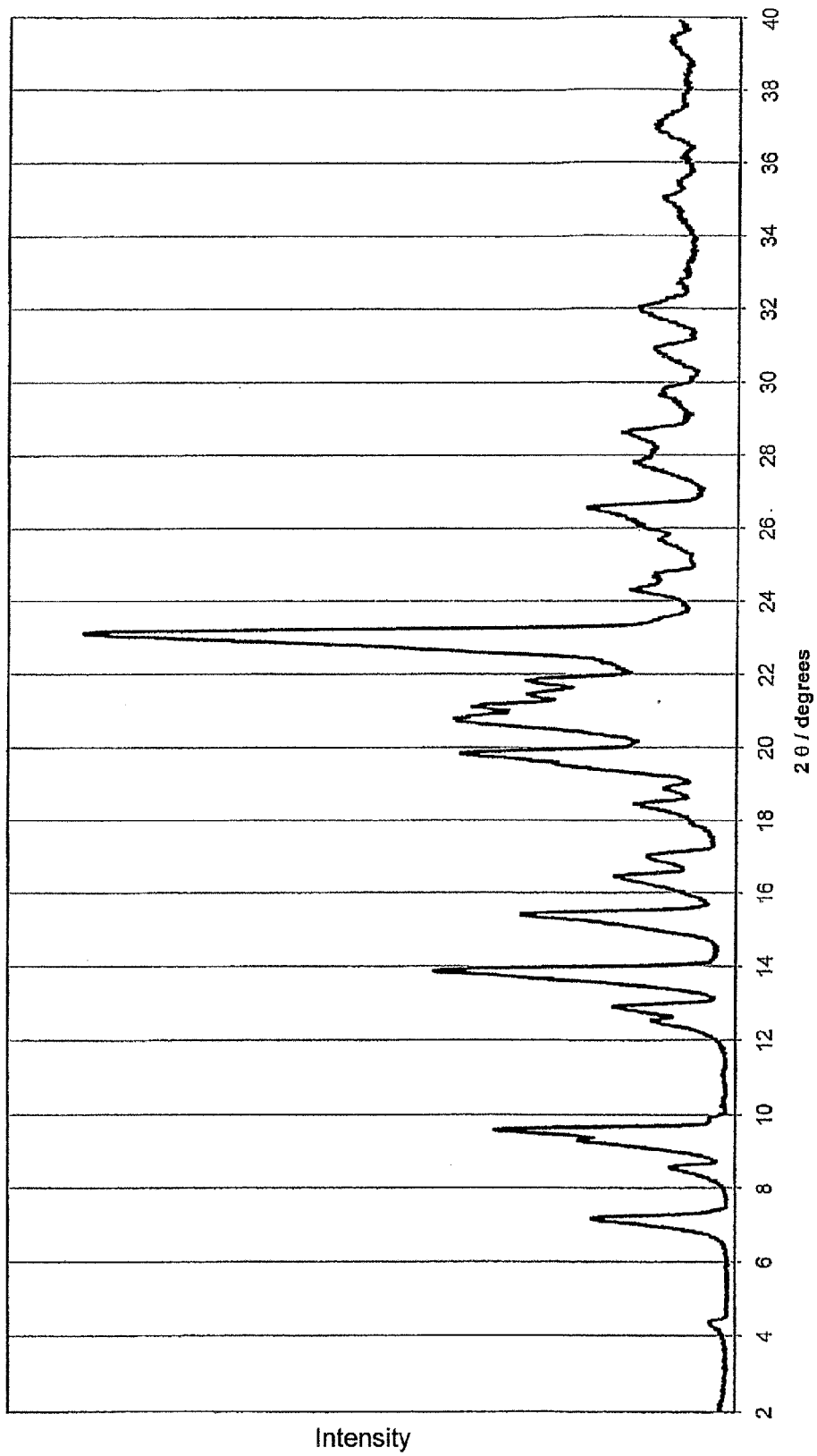
FIG. 1 illustrates the polymorphic form III which is characterized by X-ray-powder diffraction.

These conventional methods have various disadvantages. Reagents, such as Raney Nickel are used in the conventional methods, which make it necessary to separate and purify the intermediate product, before it can be used in the next stage. Combining individual stages in a multi-stage continuous process is, thus, in the majority of cases not possible. Moreover, it is also problematic to use Raney Nickel for reasons of environmental conservation, due to the toxicity and lack of safety. The same is true regarding the use of 2-chloro-benzonitrile, that is used as the starting compound for the preparation of the primary amines. Furthermore, it would be advantageous to increase the yield of the entire process.

Now, it is found that the above mentioned disadvantages may be overcome, by using harmless and cheaper starting compounds and intermediates so as to carry out the process with only two separate processing steps and also greatly enhance the yield of the active substance. This is achieved according to the present invention, by using, in lieu of the primary amine i.e. (S)-1-(2-piperidino-phenyl)-1-alkylamines, or (S)-1-(2-piperidino-phenyl)-1-benzylamine, a secondary amine having the secondary amino nitrogen provided with a nucleofuge. Similarly, one can also use an appropriate salt of such a compound. This secondary amine or the appropriate salt of the compound thereof can be reacted with an appropriate substituted phenyl acetic acid, resulting in the cleavage of the nucleofuge, such that the carboxyl groups, which are bonded at the phenyl ring and optionally protected as ester groups, are released from the compound obtained. For preparing the secondary amine, one can start with a nonhazardous halobenzaldehyde, such as 2-fluoro-benzaldehyde, whereby an additional hydrogenation step can be avoided. The individual steps of the process can be conducted directly one after the other in a continuous manner without preparing the intermediate product separately. The process according to the invention, thus, demonstrates only two separate processing steps starting from the commercially available 2-halobenzaldehyde till the final product.

The positive effect of the protective group and the nucleofuge respectively bonded at the amino nitrogen is surprising. Since the primary amines are clearly more reactive than the secondary amines provided with a nucleofuge or a protective group, it was to be assumed that carrying out the reaction according to the instant invention would decrease the rate of the reaction and the yields would also reduce. Surprisingly, the opposite is demonstrated. Despite the substituent at the amino nitrogen, considerably shorter reaction time and higher yields could be achieved as compared to the conventional methods.

The present invention is defined in the patent claims. Specifically, the invention concerns a method for preparing (S)(+)phenylacetic acid derivatives having the general formula (I):

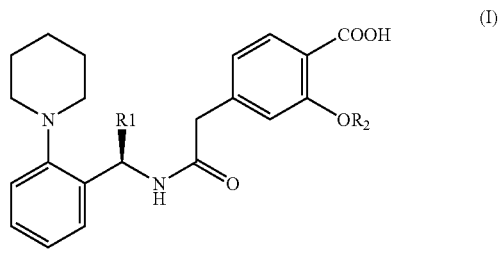

wherein $R_1$ is a linear or branched alkyl group with 1-6 carbon atoms or optionally substituted benzyl group, and $R_2$ is a methyl, ethyl or propyl group, said method is characterised in that (S)-1-(2-piperidino-phenyl)amine or a compound having the general formula (II):

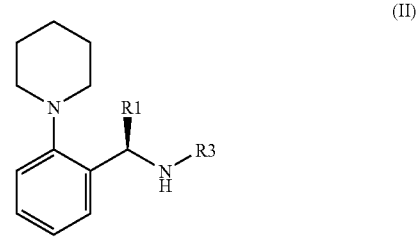

where $R_1$ is as defined above, and $R_3$ is a nucleofuge, or a suitable salt of a compound having the general formula (II), is reacted with a compound having the general formula (III):

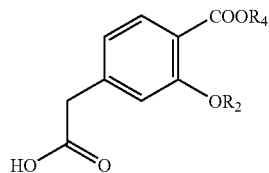

where $R_2$ is the same as above, and
$R_4$ is hydrogen or protective group that can be removed hydrolytically, and thereafter the protective group $R_4$, which may be present and which can be removed hydrolytically, is removed.

$R_1$ is preferably a methyl, ethyl, n-propyl, n-butyl, n-pentyl, n-hexyl, 2-methyl-propyl or benzyl group, preferably 2-methyl-propyl group.

$R_2$ is preferably an ethyl group.

$R_3$ as nucleofuge is preferably a benzyl or substituted benzyl or allyl group, preferably substituted benzyl group, which is substituted at the phenyl ring by at least one electronegative, electron-supplying substituent. Such electronegative substituents are, for instance, $(C_{1-4})$-alkoxy, preferably methoxy or ethoxy, or chlorine. Similarly, benzyl radicals can be used as nucleofuges, which bring to the methylene ($-CH_2-$) of the benzyl radical, a suitable, preferably electronegative, electron-supplying, substituent, such as for instance $(C_{1-4})$-alkyl or optionally substituted phenyl, whereby in the latter case the methylene preferably shows two identical optionally substituted phenyl rings. Benzyl, which is substituted by at least one methoxy group at the phenyl ring is preferred. $R_3$ preferably stands for 2-methoxybenzyl, 4-methoxybenzyl, or 2,4-dimethoxybenzyl.

$R_4$ preferably is hydrogen, methyl, ethyl, butyl, or propyl group, as well as optionally substituted benzyl group, preferably ethyl, butyl, propyl or benzyl group.

The reaction of the compounds of the formula (II) with a compound having the formula (III) can be done under the reaction environment which is known from the analogous transformations. The substituent $R_3$ of the compound from the general formula (II) is stable under the alkaline conditions, and can be removed or substituted in an acidic medium. For coupling to the amide linkage, one preferably conducts the conversion in an organic solvent, such as benzol, toluene, tetrahydrofuran, ethyl acetate, methyl acetate, acetonitrile, dimethylformamide, preferably in an aprotic solvent, preferably in a polar aprotic solvent. If necessary, at an elevated temperature, one then separates the nucleofuge in the presence of an acid, such as hydrochloric acid, sulphuric acid, perchloric acid, trifluoroacetic acid, methanesulphonic acid, chlorosulphonic acid, p-toluenesulphonic acid, benzolsulphonic acid, preferably methanesulphonic acid, chlorosulphonic acid and/or p-toluenesulphonic acid, preferably methanesulphonic acid. In case, if required, the reaction is conducted at reflux temperature, one uses for this reaction, an acidic value (pH) of, preferably less than 2 (pH<2), as such values are obtained in the presence of the acids referred to above, preferably the sulphonic acids. The molar ratio of the compound, or a suitable salt of the compound of the formula (II), to the acid used, lies primarily in the range of 1:1 to 1:50, particularly in the range of 1:1 to 1:5.

Salts of the compounds of the formula (II), used for the reaction with a compound of the formula (III), as described earlier, are especially the salts of the compounds having the chiral acids, which, by themselves, are optically active (marked here with "A"), such as optically active carboxylic acids, e.g. mandelic acid [$C_6H_5$—*CH(OH)COOH] which is optionally substituted at the phenyl ring, optically active camphorsulphonic acid, optically active tartaric acid and optically active substituted tartaric acid or also optically active phosphoric acid, e.g. 1,1'-binaphthalin-2,2'-diyl-phosphoric acid. These salts are obtained as intermediate products while preparing the compounds having the formula (II) as per the invention. If one treats the compound, having the formula (II) present in the salt form, in the conventional way with an alkali, then one gets the compound of the formula (II). Suitable salts of the compounds of the formula (II) needed for the reaction with the compound having the formula (III) are especially the salts of the optically active camphorsulphonic acids and the optically active phosphoric acids.

The (S)-1-(2-piperidino-phenyl) amine or the compound having the general formula (II) is produced, as per the following reaction scheme wherein

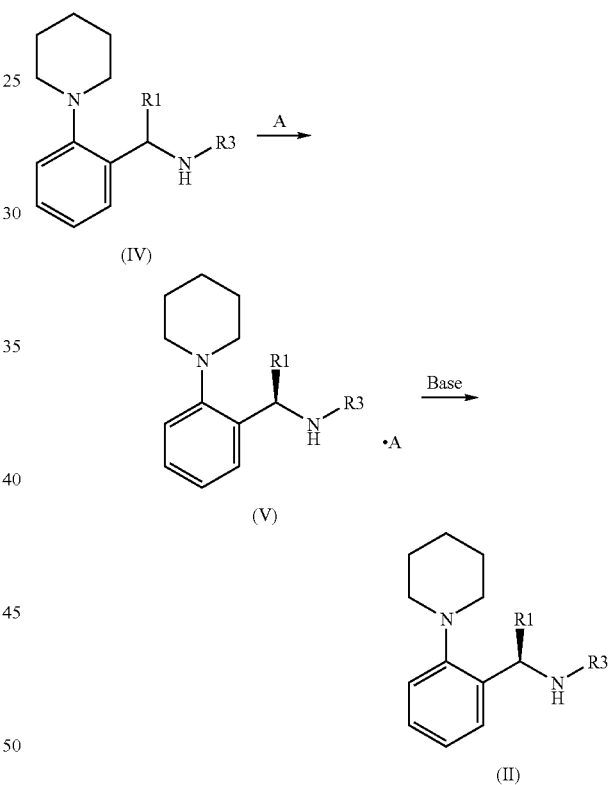

a racemic mixture of compounds having the general formula (IV) are reacted with a chiral acid "A", by a conventional method, such that the appropriate acid salt is obtained in accordance with the formula (V). This salt is removed and converted to the (S)-1-(2-piperidino-phenyl) amine or the compound having the general formula (II) in the alkaline medium. In the reaction scheme given above, the substituents $R_1$ and $R_3$ have the values as stated above.

In this sense, the present invention concerns a method for preparing the compounds having the general formula (II), which is characterised by the fact that one converts a racemic mixture of compounds of general formula (IV) by a conventional method by reacting with a chiral acid "A", such that the suitable salt is obtained in accordance with the formula (V).

Subsequently, it is removed and converted to the compound having the general formula (II) in the alkaline medium.

"A" stands for the optically active chiral acid as defined above, preferably a carboxylic acid. Substituted optically active mandelic acids are, for instance, o-chloromandelic acid, p-chlormandelic acid, p-bromomandelic acid. Substituted optically active tartaric acids are the tartaric acids esterified at the hydroxyl groups, such as di-O,O'-p-toluyl-tartaric acid or di-O,O'-pivaloyl-tartaric acid. Preferred are the optically active mandelic acid, o-chloromandelic acid, p-chloromandelic acid, p-bromomandelic acid, particularly mandelic acid and o-chloromandelic acid. If one treats the racemic mixture conforming to the general formula (IV) with a chiral acid "A", then the salt of the formula (V) is formed, from which the amine having the formula (II) can be obtained with a high enantiomeric purity. The suitable chiral acid is either laevo- or dextrorotatory. Thus, for mandelic acid and the 2-chloromandelic acid, one preferably uses the laevorotatory form. The fact whether the laevo- or the dextrorotatory form is optimum for the separation of the racemic mixture or not, can be ascertained easily by a person skilled in the art for the respective acids used.

The described separation, of the racemic mixture of the compounds having the general formula (IV) with a chiral acid "A", is new, as also the suitable salt conforming to the formula (V). Further, it is surprising that the salt is formed with the secondary amine so quickly and with such a high yield and high purity.

In this sense the present invention concerns the compounds of the general formula (V) present as salt:

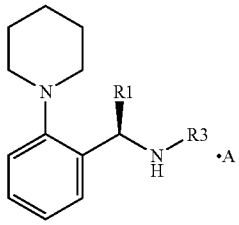

(V)

wherein $R_1$, $R_3$ and A relate to the respective groups given above.

The present invention also pertains to a technique for preparing the compounds having the general formula (V), which is characterised by the fact that one converts a racemic mixture of compounds having the general formula (IV):

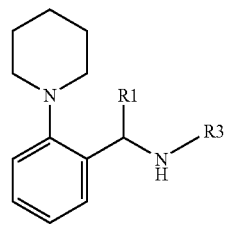

(IV)

with a chiral acid "A", whereby the suitable salt is obtained according to the general formula (V) and the compound of the formula (V) is isolated (racemate splitting).

As solvent for the racemate splitting, one preferably uses the low-molecular weight alcohols such as methanol, ethanol, isopropanol, butanol (also mixed with water to the extent possible), low-molecular weight ketones such as dimethylketone, diethylketone, methylethylketone (optionally mixed with water to the extent possible), $(C_1-C_6)$-carboxylic acid esterified preferably with low-molecular weight alcohols, cyclic and non-cyclic ethers, such as diethylether, dimethoxyethane, 1,4-dioxane (also mixed with water to the extent possible) and/or $C_1-C_6$-nitrile, such as acetonitrile, propionitrile or butyronitrile. Preferably, the molar ratio of amine [compound of the formula (IV)]: chiral acid during the preparation of the salt and the precipitation lies in the range of about 3:1 to 1:10, particularly in the range of about 2:1 to 1:2. The acidic value (pH) during the salt formation and the precipitation lies preferably in the range of 3.5 to 10.0, particularly in the range of 5.0 to 7.5. The reaction temperature is relatively non-critical and can generally lie in the range of 0° C. to 100° C., whereby the salt which forms at high temperature gets crystallised or precipitated on cooling.

Further, the present invention pertains to a technique for preparing the compounds of the general formula (II), which is characterised by the fact that one treats a salt of the general formula (V) with a base, preferably with alkali and thus converts it to the compound of the general formula (II).

The racemic mixture of the compounds of the general formula (IV) are prepared, for instance, by starting with 2-fluoro-benzaldehyde and substituting the fluorine atom with piperidine nucleophile. The resultant product is converted to imine with p-methoxybenzylamine, and the imine obtained thus, is subsequently reacted with a Grignard reagent, whereby the racemic mixture of the compounds of the general formula (IV) is obtained. This mixture is then, as already described, converted with a chiral acid "A". The entire method starting from 2-fluorobenzaldehyde till the formation of the compounds of the formula (V) can be carried out without the isolation of any intermediate product, whereby the yield is much higher than the yield of the methods described in the prior art.

The present invention also pertains to the hitherto unknown polymorphic forms of Repaglinid. From the literature, two polymorphic forms of Repaglinid are known, namely one form (called here as the polymorphic form I) with a melting point of 132-133° C. and another polymorphic form (called here as polymorphic form II) with a melting point of 102° C. It has now been found that four more polymorphic or pseudo-polymorphic forms of Repaglinid exist. These other polymorphic forms have specific technical advantages, such as different solution behaviours that is, in part with a better solubility and in part can also be formulated in a better way than the known forms.

The polymorphic form III with a melting point of 118-119° C. is obtained, for instance, by crystallising from a mixture of 2.0 parts of isopropanol and 20 parts of cyclohexane. The polymorphic form III is characterised by X-ray-powder diffraction (CuK$_\alpha$ radiation, λ=1.5418 Å) as shown in FIG. 1.

Figure 2:
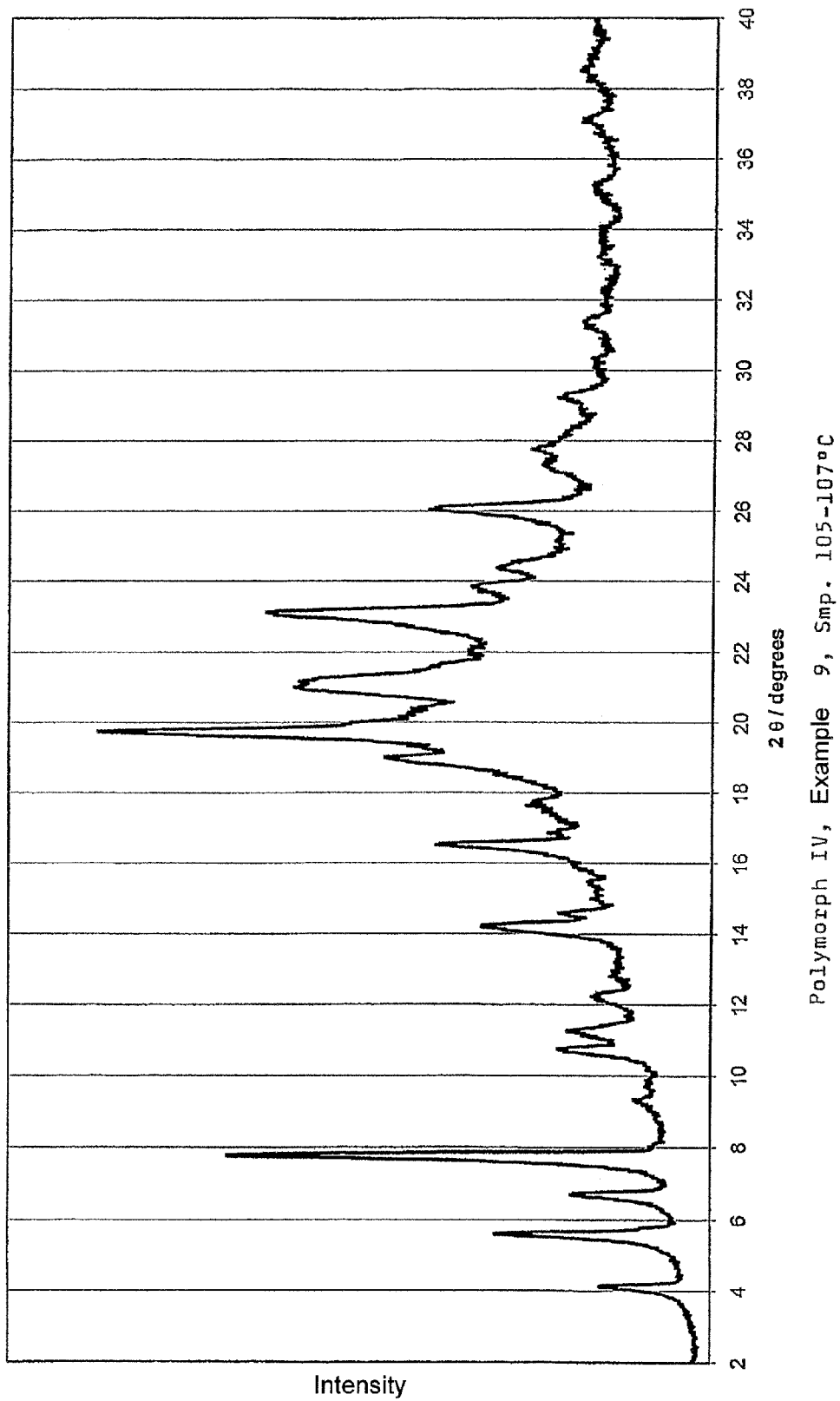
FIG. 2 illustrates the polymorphic form IV which is characterized by X-ray-powder diffraction.

The polymorphic form IV with a melting point of 105-107° C. is obtained, for instance, by crystallising from a mixture of 30 parts of tert-butylmethylether and 27 parts of toluene. The polymorphic form IV is characterised by X-ray powder diffraction (CuK$_\alpha$ radiation, λ=1.5418 Å) as shown in FIG. 2.

Figure 3:
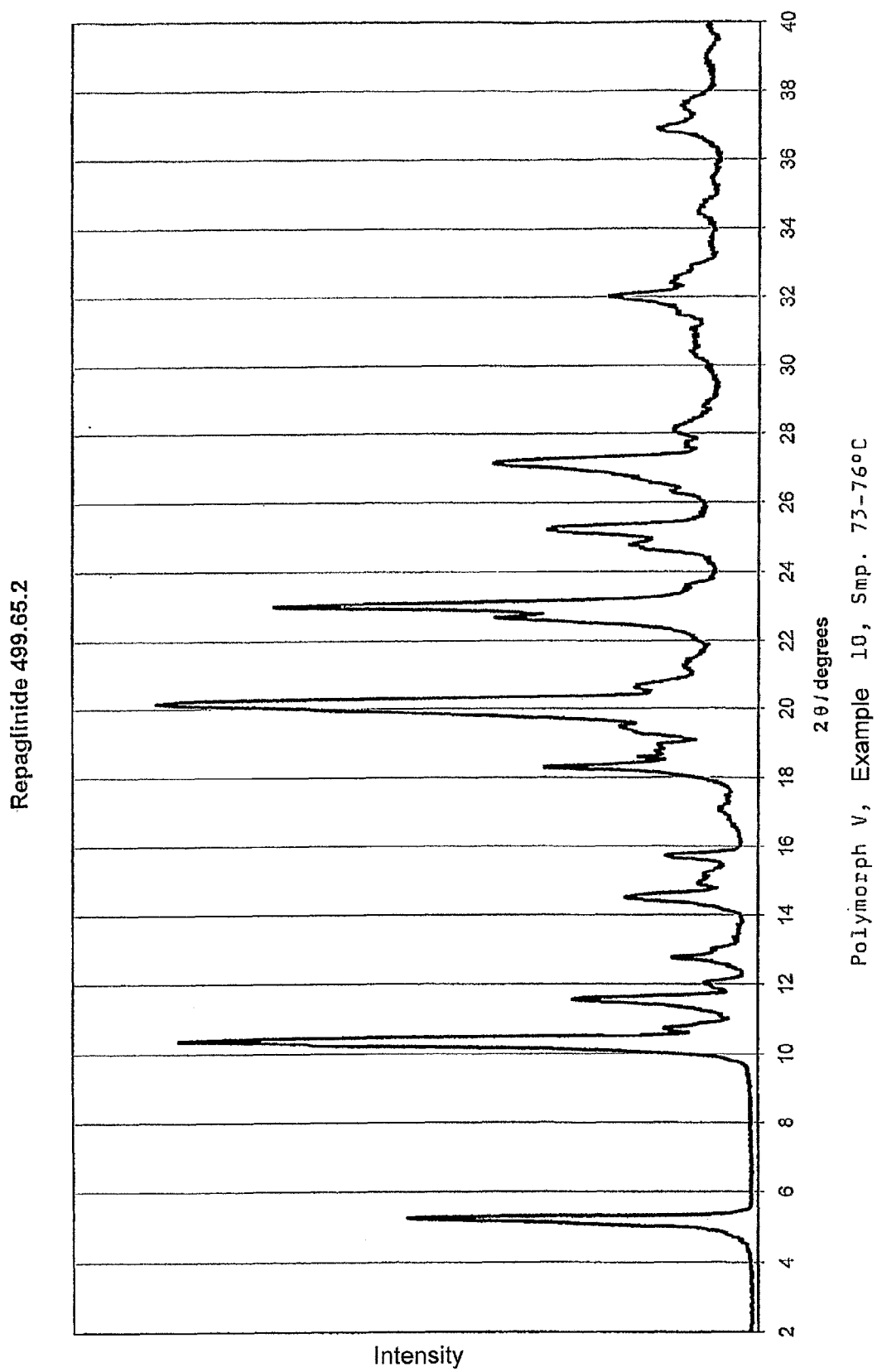
FIG. 3 illustrates the polymorphic form V which is characterized by X-ray-powder diffraction.

The polymorphic form V with a melting point of 73-76° C. is obtained, for instance, by crystallising from methanol. This polymorphic form V represents a hemi-methanolate i.e. for each two molecules of repaglinid the form contains one molecule of methanol. The polymorphic form V is characterised by X-ray-powder diffraction (CuK$_\alpha$ radiation, λ=1.5418 Å) as shown in FIG. 3.

Figure 4:
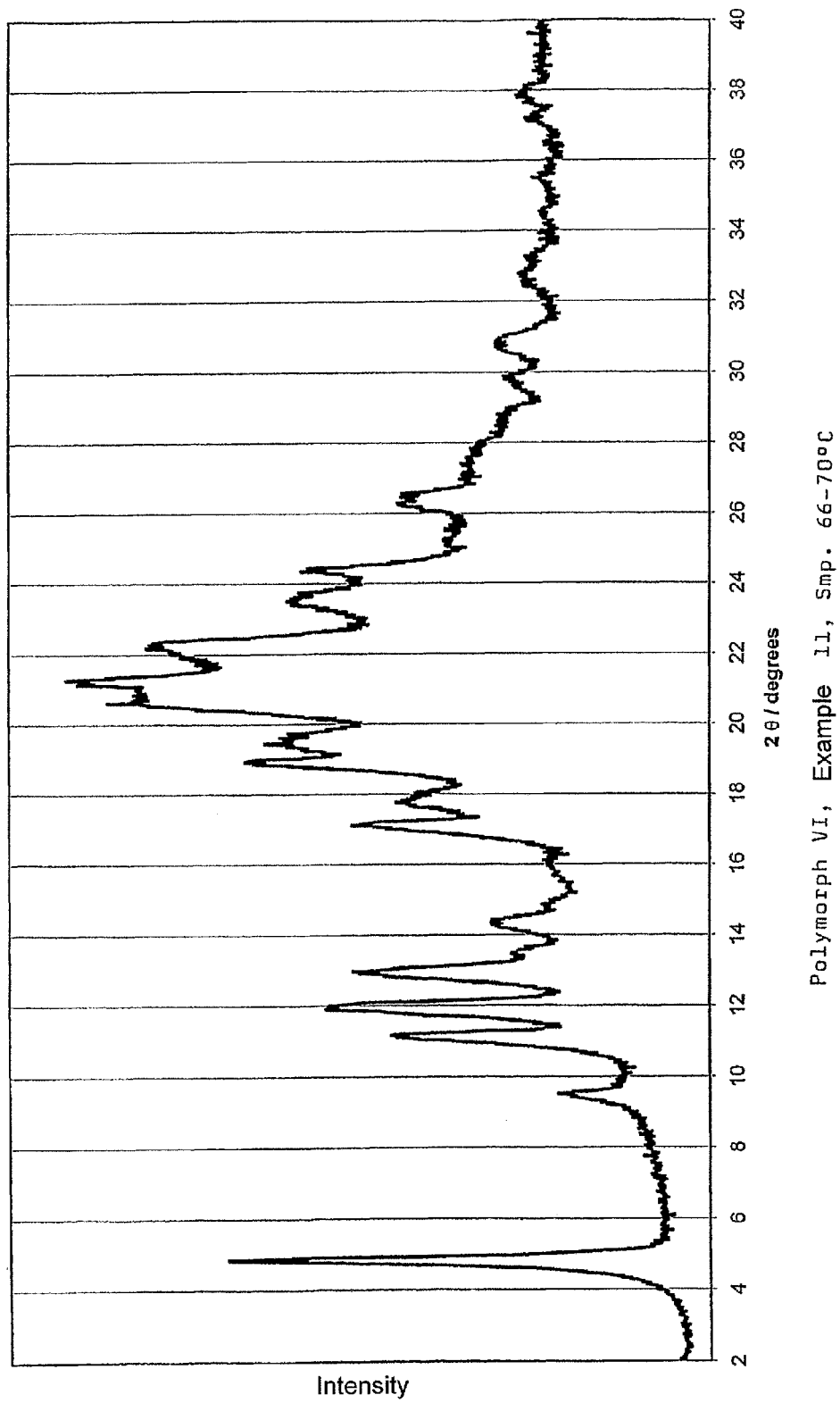
FIG. 4 illustrates the polymorphic form VI which is characterized by X-ray-powder diffraction.
Figure 5:
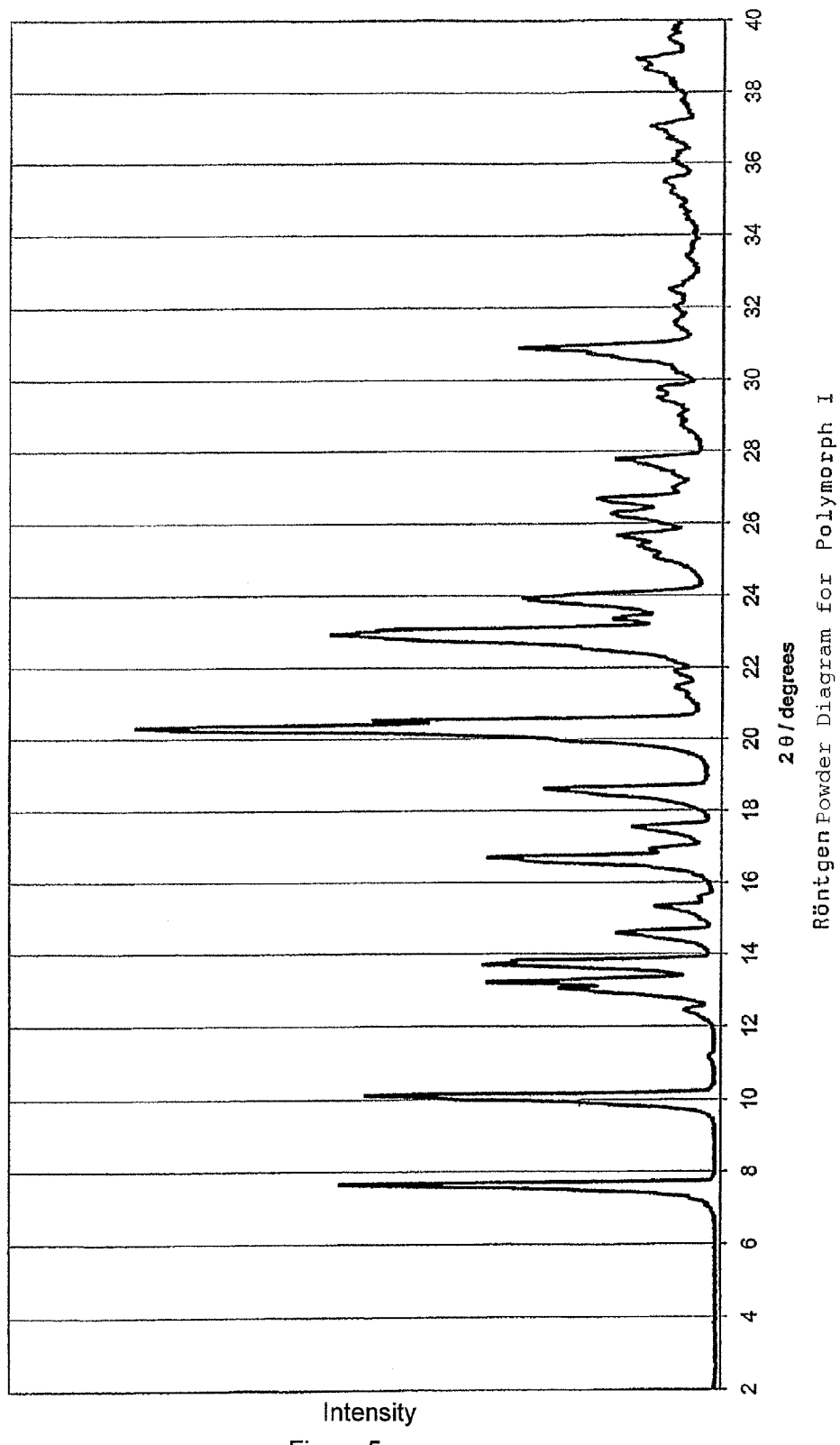
FIG. 5 illustrates a Rontgen powder diagram of the polymorphic form I.

The polymorphic form VI with a melting point of 66-70° C. is obtained, for instance, by crystallising from 50 parts of methanol and 10 parts water. This polymorphic form VI represents a hydrate, in which 0.25 equivalent water is present for one molecule of repaglinid. The polymorphic form VI is characterised by X-ray-powder diffraction (CuK$_\alpha$ radiation, $\lambda$=1.5418 Å) as shown in FIG. 4.

The following examples illustrate the invention.

EXAMPLE 1

[(S)-1-(2-piperidino-phenyl)-3-methyl-1-butyl-N-4-methoxybenzyl-ammonium-L-mandelate]

168 g (1.21 mole) of potassium carbonate are heated in a mixture of 100 ml toluene, 100 ml dimethylformamide (DMF) and 130 g (1.0 mole) of 2-fluorobenzaldehyde at reflux and are reacted with 102 g (1.2 mole) of piperidine. After 4 hours the product obtained is hydrolysed with 300 ml water and the phases are separated. To the organic phase one adds 140 g 4-methoxybenzylamine (1.0 mole) and separates the water formed with the help of azeotropic distillation. The solution obtained is added to a freshly prepared solution of 420 g isobutyl-magnesium bromide (2.6 mole) in 900 ml ether. After complete conversion, the mixture is then hydrolysed with a mixture comprising of 184.5 g glacial acetic acid and 603 g water. The separated organic phase is reacted with 111.2 g (0.73 mole) L-mandelic acid as well as 900 ml ethyl acetate and heated at reflux. Upon cooling, crystals of the desired product separate out at about 50° C. The mixture is filtered at room temperature. Yield: 210 g product. In order to increase the enantiomeric excess to >95%, the product is re-crystallised once from a mixture comprising of 525 ml water and 525 ml methanol. Yield: 182 g (30% with reference to 2-fluorobenzaldehyde).

EXAMPLE 2

[(S)-1-(2-piperidino-phenyl)-1-butyl-N-4-methoxy-benzyl-ammonium-L-mandelate]

46.2 g (0.33 mole) of potassium carbonate are heated at reflux in a mixture comprising of 25 ml toluene, 25 ml dimethylformamide (DMF) and 35.7 g (0.28 mole) of 2-fluorobenzaldehyde and reacted with 28.0 g (0.33 mole) of piperidine. After 4 hours the product obtained is hydrolysed with 300 ml water and the phases are separated. To the organic phase, one adds 38.5 g of 4-methoxybenzylamine (0.28 mole) and separates the water formed with the help of azeotropic distillation. The solution obtained is added to a freshly prepared solution of 90 g n-propyl magnesium bromide (0.61 mole) in 630 ml of ether. After a complete conversion, a hydrolysis is done with a mixture comprising of 35.1 g glacial acetic acid and 130 g of water. The separated organic phase is reacted with 40.7 g (0.27 mole) of L-mandelic acid as well as 385 ml of acetonitrile and heated to reflux temperature. Upon cooling, the crystals of the desired product separate out at about 50° C. The crystals are filtered out at room temperature. Yield: 46.9 g of the desired product. In order to increase the enantiomeric excess to >95%, the product is recrystallised with a mixture comprising of 100 ml water and 100 ml ethanol. Yield: 41.8 g (30% with reference to 2-fluorobenzaldehyde).

EXAMPLE 3

[(S)-1-(2-piperidino-phenyl)-3-methyl-1-butyl-N-benzyl-ammonium-L-mandelate]

1.68 g (0.012 mole) of potassium carbonate are heated in a mixture comprising of 4 ml toluene, 4 ml DMF and 1.3 g (0.01 mol) of 2-fluorobenzaldehyde at reflux and reacted with 1.02 g (0.012 mole) of piperidine. After 4 hours the product obtained is hydrolysed with 3.0 ml water and the phases are separated. To the organic phase, one adds 1.07 g benzylamine (0.01 mole) and separates out the water formed with the help of azeotropic distillation. The solution thus obtained is added to a freshly prepared solution of 4.20 g isobutyl magnesium bromide (0.026 mole) in 9 ml ether. After a complete conversion, a hydrolysis is done with a mixture comprising of 1.85 g glacial acetic acid and 6.0 g water. The separated organic phases are reacted with 1.1 g (0.0073 mole) L-mandelic acid as well as 9.0 ml of ethyl acetate and heated to reflux temperature. Upon cooling the crystals of the desired product separate at about 20° C., which are filtered out at room temperature. Yield: 0.77 g of product (enantiomeric purity: 41%. Yield 13% with respect to 2-fluoro-benzaldehyde). In order to increase the enantiomeric excess to >95%, the product is crystallised thrice from a mixture comprising of 2.5 ml of water and 2.5 ml of methanol.

EXAMPLE 4

[(S)(+)-2-ethoxy-4-[N-[1-(2-piperidino-phenyl)-3-methyl-1-butyl]amino carbonyl methyl]benzoic acid]

100 g (0.19 mole) of (S)-1-(2-piperidino-phenyl)-3-methyl-1-butyl-N-4-methoxybenzyl-ammonium-L-mandelate are added to 600 ml toluene and 300 g 4% caustic soda (0.3 mole). The organic phase is separated and is added to a well-stirred mixture of 49.1 g (0.19 mole) 3-ethoxy-4-ethoxy-carbonyl phenyl acetic acid and 43.2 g (0.27 mole) 1,1'-carbonyl-diimidazole (CDI) in a mixture comprising of 350 ml toluene and 200 ml acetonitrile. After the coupling reaction is completed, one adds 300 ml water and separates the phases. To the organic phase one first adds 20 ml of water, 230 g (2.0 mole) of trifluoroacetic acid and then adds 70 g (0.73 mole) of methanesulphonic acid at reflux temperature. As soon as the conversion is complete, one adds 200 ml water and separates the arising three-phase system. The middle phase is diluted with 100 ml ethanol as well as with 250 ml toluene and with 421 g of about 17% caustic potash (1.3 mole). The phases are separated. The aqueous phase is acidified with hydrochloric acid to a pH value of 5.1 and is shaken with 300 ml ethyl acetate. The ethyl acetate phase is concentrated to about a third. Upon cooling, the product precipitates out. It is filtered out at room temperature. Yield: 64.4 g of colourless crystals (73.7% with respect to (S)-1-(2-piperidino-phenyl)-3-methyl-1-butyl-N-4-methoxy-benzyl-ammonium-L-mandelate). In order to increase the purity of the product to >99.8%, the raw product is recrystallised with a mixture of 200 ml acetonitrile and 100 ml water. Yield 61.2 g (70%). The polymorph I with a melting point of 132-133° C. is obtained.

EXAMPLE 5

[(S)(+)-2-ethoxy-4-[N-[1-(2-piperidino-phenyl)-1-pentyl]amino-carbonyl-methyl]benzoic acid]

7.68 g (0.013 mole) of a concentrated solution of (S)-1-(2-piperidino-phenyl)-1-pentyl-N-4-methoxy-benzylamine in toluene (content of optically pure amine around 65%) are added to a well-stirred mixture of 4.66 g (0.018 mole) of 3-ethoxy-4-ethoxycarbonyl-phenyl acetic acid and 5.03 g (0.031 mole) of 1,1'-carbonyl-diimidazole in a mixture comprising of 15 ml toluene and 10 ml acetonitrile. After the coupling reaction is finished, one adds 15 ml of water to the reaction mixture and separates the phases. To the organic phase, one first adds 2.0 ml of water, 23.8 g (0.21 mole) of trifluoroacetic acid and subsequently at reflux temperature, 7.36 g (0.077 mole) of methanesulphonic acid. As soon as the conversion is complete, one adds 20 ml of water and separates the arising two-phase system. The upper phase is diluted with 10 ml of ethanol and with 44.7 g of about 17% caustic potash (0.13 mole). The phases are separated and the aqueous phase is acidified with hydrochloric acid to a pH value of 5.1 and is shaken with 30 ml of ethyl acetate. The ethyl acetate phase is left standing, till the product crystallises out. Yield: 6.14 g, slightly brown crystals (almost quantitative, with reference to (S)-1-(2-piperidino-phenyl)-1-pentyl-N-4-methoxy-benzylamine).

EXAMPLE 6

[potassium-(S)(+)-2-ethoxy-4-[N-[1-(2-piperidino-phenyl)-1-butyl]amino-carbonyl-methyl]benzoate]

7.26 g (0.018 mole) of (S)-1-(2-piperidino-phenyl)-1-butyl-N-4-methoxybenzylamine are added to a well-stirred mixture of 4.61 g (0.018 mole) of 3-ethoxy-4-ethoxycarbonyl-phenyl acetic acid and 5.02 g (0.031 mole) 1,1'-carbonyl-diimidazole in a mixture comprising of 15 ml toluene and 10 ml of acetonitrile. After the coupling reaction is completed, one adds 15 ml water and separates the phases obtained. To the organic phase, one first adds 2.0 ml of water, 24.0 g (0.21 mole) of trifluoroacetic acid and then 7.05 g (0.073 mole) of methane sulphonic acid at reflux temperature. As soon as the conversion is complete, one adds 20 ml of water and separates the arising two-phase system. The upper phase is diluted with 10 ml ethanol and with 43.3 g of about 17% caustic potash (0.13 mole). From the aqueous phase, a colourless solid separates out, which is filtered out and washed with 20 ml toluene. Yield: 6.17 g (content of product as potassium salt: approx. 92%, yield 69% with reference to (S)-1-(2-piperidino-phenyl)-1-butyl-N-4-methoxybenzylamine).

EXAMPLE 7

[(S)(+)-2-ethoxy-4-[N-[1-(2-piperidino-phenyl)-3-methyl-1-butyl]amino-carbonyl-methyl]benzoic acid]

1.0 g (0.002 Mol) of (S)-1-(2-piperidino-phenyl)-3-methyl-1-butyl-N-benzylammonium-L-mandelate is solubilised in 6.0 ml of toluene and 3.0 g of 4% caustic soda (0.003 mole). The organic phase is separated and added to a well-stirred mixture of 0.52 g (0.002 mole) of 3-ethoxy-4-ethoxy-carbonyl phenyl acetic acid and 0.43 g (0.0027 mole) of 1,1'-carbonyl diimidazole in a mixture comprising of 3.5 ml toluene and 2.0 ml acetonitrile. After the coupling reaction is complete, one adds 3.0 ml of water and separates the phases. To the organic phase one adds first 0.2 ml of water, 2.3 g (0.02 mole) of trifluoroacetic acid and then 0.7 g (0.007 mole) of methane sulphonic acid at reflux temperature. As soon as the conversion is complete, one adds 2.0 ml water and separates the arising three-phase system. The middle phase is diluted with 1.0 ml ethanol as well as 2.5 ml toluene and with 4.21 g of approx. 17% caustic potash (0.013 mole). The phases are separated and the aqueous phase is acidified with hydrochloric acid to a pH value of 5.1 and shaken with 10 ml ethyl acetate. The ethyl acetate phase is concentrated to about a third. Upon cooling, the product crystallises and is then filtered out at room temperature. Yield: 0.15 g colourless crystals (16.2% calculated on (S)-1-(2-piperidino-phenyl)-3-methyl-1-butyl-N-benzylammonium-L-mandelate).

EXAMPLE 8

Polymorph III 4.66 g of (S)(+)-2-ethoxy-4-[N-[1-(2-piperidino-phenyl)-3-methyl-1-butyl)amino-carbonyl-methyl]benzoic acid are crystallised in a mixture of 2.0 ml of isopropanol and 20 ml of cyclohexane. One gets 2.54 g (55%) of a colourless solid with a melting point of 118-119° C.

EXAMPLE 9

Polymorph IV 6.0 g of (S)(+)-2-ethoxy-4-[N-[1-(2-piperidino-phenyl)-3-methyl-1-butyl]amino-carbonyl-methyl]benzoic acid is heated in a mixture comprising of 30 g of tert-butylmethyl-ether and 27 g of toluene, till the solid dissolves completely. It is cooled to 0° C. and the precipitated product is filtered out. One gets 5.07 g of a colourless solid (85%) with a melting point of 105-107° C.

EXAMPLE 10

Polymorph V 3.0 g of (S)(+)-2-ethoxy-4-[N-[1-(2-piperidino-phenyl)-3-methyl-1-butyl]-amino-carbonyl-methyl)benzoic acid is dissolved in 15 ml methanol. One leaves the solution for 2 days, then filters out the colourless product that has formed and dries it in vacuum. The solid melts at 73-76° C. and still contains 3.5% methanol, for which reason the structure of a hemimethanolate is assigned to it. Yield: 2.21 g (74%).

EXAMPLE 11

Polymorph VI 6.0 g of (S)(+)-2-ethoxy-4-[N-[1-(2-piperidino-phenyl)-3-methyl-1-butyl]-amino-carbonyl-methyl]benzoic acid is heated in a mixture comprising of 50 g methanol and 10 g water, till the solid dissolves completely. It is cooled to 20° C. and the product formed is filtered out. One gets 5.03 g of a colourless solid with a melting point of 66-70° C., which still contains 0.8% water, for which reason the structure of a 0.25 hydrate is assigned to it. Yield: 84%.

The invention claimed is:
1. Method for preparing (S)(+)phenyl-acetic acid derivatives having the general formula (I):

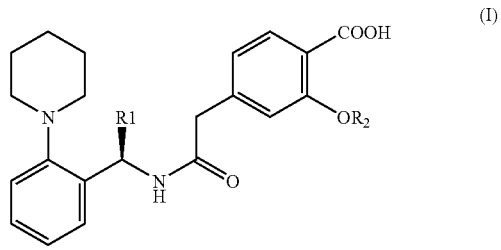

wherein
R$_1$ is a methyl, ethyl, n-propyl, n-butyl, n-pentyl, n-hexyl, 2-methyl-propyl or benzyl group, and
R$_2$ is a methyl, ethyl or propyl group, characterized in that a compound having the general formula (II):

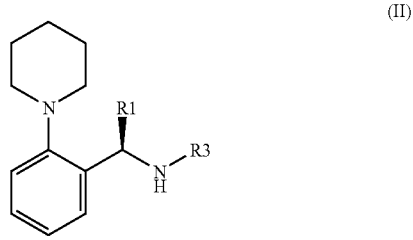

(II)

wherein R$_1$ is as given above, and
R$_3$ is a benzyl or substituted benzyl or allyl group which is substituted at the phenyl ring by at least one electronegative, electron supplying substituent, or a substituted benzyl group, which is substituted at methylene by one electronegative, or an electron-supplying substituent, or a suitable salt of a compound having the general formula (II), is reacted with a compound having the general formula (III):

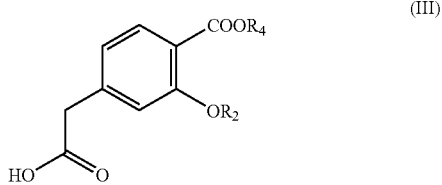

(III)

wherein R$_2$ is as given above, and
R$_4$ is hydrogen or a protective group that can be removed hydrolytically, and the hydrolytically removable protective group R$_4$ that may be present is removed thereafter.

2. Method as per claim 1, characterised in that:
R$_2$ is ethyl group,
R$_3$ is benzyl which is substituted at the phenyl ring by at least one methoxy-group, and
R$_4$ is hydrogen, methyl, ethyl, butyl, propyl or optionally substituted benzyl.

3. Method as per claim 1, characterised in that R$_1$ is 2-methyl-propyl group, R$_2$ is ethyl group, R$_3$ is 2-methoxybenzyl, 4-methoxybenzyl, or 2,4-dimethoxybenzyl group, and R$_4$ is hydrogen, ethyl, butyl, propyl or benzyl group.

4. Method according to claim 1, characterised in that coupling is carried out with the amide linkage in an organic solvent, and thereafter the nucleofuges are removed in the presence of an acid, optionally at an acidic value of less than 2, and if need be at an elevated temperature.

5. Method according to claim 1, characterised in that the reaction is carried out with a salt of the formula (II) and the salt of formula (II) is formed on reaction with an optically active chiral acid "A", selected from the group of: optically active carboxylic acid, optically active camphorsulphonic acid, optically active tartaric acid, optically active substituted tartaric acid, optically active phosphoric acid.

6. Method according to claim 4 where said organic solvent is a aprotic solvent, and where said acid is selected from the group of: trifluoroacetic acid, methanesulphonic acid, chlorosulfonic acid, and/or p-toluenesulfonic acid.

7. Method according to claim 5 where said optically active carboxylic acid and said optically active phosphoric acid is selected from the group of: mandelic acid, mandelic acid which is substituted at the phenyl ring, optically active mandelic acid, p-chloromandelic acid, p-bromomandelic acid or o-chloromandelic acid.

8. Method according to claim 2, characterised in that coupling is carried out with the amide linkage in an organic solvent, and thereafter the nucleofuges are removed in the presence of an acid optionally at an acidic value of less than 2, and if need be at an elevated temperature.

9. Method according to claim 3, characterised in that coupling is carried out with the amide linkage in an organic solvent, and thereafter the nucleofuges are removed in the presence of an acid, optionally at an acidic value of less than 2, and if need be at an elevated temperature.

10. Method according to claim 2, characterised in that the reaction is carried out with a salt of the formula (II) and the salt of formula (II) is formed on reaction with an optically active chiral acid "A" selected from the group of: optically active carboxylic acid, optically active camphorsulphonic acid, optically active tartaric acid, optically active substituted tartaric acid, and optically active phosphoric acid.

11. Method according to claim 3, characterised in that the reaction is carried out with a salt of the formula (II) and the salt of formula (II) is formed on reaction with an optically active chiral acid "A" selected from the group of: optically active carboxylic acid, optically active camphorsulphonic acid, optically active tartaric acid, optically active substituted tartaric acid, and optically active phosphoric acid.

12. Method according to claim 4, characterised in that the reaction is carried out with a salt of the formula (II) and the salt of formula (II) is formed on reaction with an optically active chiral acid "A" selected from the group of: optically active carboxylic acid, optically active camphorsulphonic acid, optically active tartaric acid, optically active substituted tartaric acid, and optically active phosphoric acid.

* * * * *